(12) United States Patent
Kalogianni

(10) Patent No.: US 9,372,178 B2
(45) Date of Patent: Jun. 21, 2016

(54) APPARATUSES AND METHODS FOR THE MEASUREMENT OF LIQUID PROPERTIES AND PARTICULARLY FRYING OIL QUALITY

(71) Applicant: Eleni Kalogianni, Thessaloniki (GR)

(72) Inventor: Eleni Kalogianni, Thessaloniki (GR)

(73) Assignee: Eleni Kalogianni, Thessaloniki (GR)

( * ) Notice: Subject to any disclaimer, the term of this patent is extended or adjusted under 35 U.S.C. 154(b) by 357 days.

(21) Appl. No.: 14/207,689

(22) Filed: Mar. 13, 2014

(65) Prior Publication Data

US 2014/0283584 A1 Sep. 25, 2014

Related U.S. Application Data

(60) Provisional application No. 61/803,472, filed on Mar. 20, 2013.

(51) Int. Cl.
*G01N 33/03* (2006.01)
*G01N 33/28* (2006.01)
*G01N 7/04* (2006.01)

(52) U.S. Cl.
CPC *G01N 33/03* (2013.01); *G01N 7/04* (2013.01); *G01N 33/2888* (2013.01)

(58) Field of Classification Search
CPC ....... G01N 33/03; G01N 33/288; G01N 7/04; G01N 11/02–11/08
USPC ...................................................... 73/54.07
See application file for complete search history.

(56) References Cited

U.S. PATENT DOCUMENTS

| | | | |
|---|---|---|---|
| 4,349,353 A | 9/1982 | Blumenthal et al. | |
| 4,654,309 A | 3/1987 | Mlinar et al. | |
| 4,721,874 A | 1/1988 | Emmert | |
| 5,670,374 A | 9/1997 | Thornton et al. | |
| 5,818,731 A | 10/1998 | Mittal et al. | |
| 6,436,713 B1 | 8/2002 | Onwumere et al. | |
| 6,459,995 B1 | 10/2002 | Collister | |
| 6,469,521 B1 | 10/2002 | Klun et al. | |
| 7,132,079 B2 | 11/2006 | Onwumere et al. | |
| 7,390,666 B2 | 6/2008 | Onwumere et al. | |
| 7,523,006 B2 | 4/2009 | Muhl et al. | |
| 7,834,646 B2 | 11/2010 | Chambon et al. | |
| 8,257,976 B2 | 9/2012 | Wei et al. | |
| 8,325,345 B2 | 12/2012 | Mahmoodi et al. | |

(Continued)

OTHER PUBLICATIONS

Kalogianni E. et al., Effect of Repeated Frying on the Viscosity, Density and Dynamic Interfacial Tension of Palm and Olive Oil, Journal of Food Engineering, 2011, 105, pp. 169-179.*

(Continued)

*Primary Examiner* — Clayton E Laballe
*Assistant Examiner* — Trevor J Bervik

(57) ABSTRACT

Apparatuses and methods for determining viscosity, surface tension and/or surface tension/viscosity ratio are presented. The methods use the measurement of liquid penetration rate in a test medium to evaluate liquid properties. In particular the methods and apparatuses can be used to determine the quality of frying or cooking oils in terms of polymer or polar compounds. The point of rejection of frying oils according to recommendations and legal limits can be determined. In one embodiment the time required for the oil to penetrate a given distance in a test strip is measured. The time is related to the above liquid (oil) properties and can be correlated to the amount of polymer and/or polar compounds in the oil sample.

26 Claims, 3 Drawing Sheets

(56) References Cited

U.S. PATENT DOCUMENTS

2011/0051141 A1* 3/2011 Mahmoodi ............ G01N 21/78
356/445
2011/0084708 A1* 4/2011 Yu .......................... G01N 33/03
324/658

OTHER PUBLICATIONS

Marmur A. et al., Characterization of Porous Media by the Kinetics of Liquid Penetration: The Vertical Capillaries Model, Journal of Colloid and Interface Science, 1997, 189, pp. 299-304.*

* cited by examiner

APPARATUSES AND METHODS FOR THE MEASUREMENT OF LIQUID PROPERTIES AND PARTICULARLY FRYING OIL QUALITY

CROSS-REFERENCE TO RELATED APPLICATIONS

This application claims the benefit of provisional application 61/803,472

STATEMENT REGARDING FEDERALLY SPONSORED RESEARCH OR DEVELOPMENT

Not applicable

THE NAMES OF THE PARTIES TO A JOINT RESEARCH AGREEMENT

Not applicable

INCORPORATION BY REFERENCE OF MATERIAL SUBMITTED ON A COMPACT DISC

Not applicable

BACKGROUND OF THE INVENTION (1) Field of the Invention

This invention relates to apparatuses and methods for determining liquid viscosity and/or surface tension. In particular it relates to apparatuses and methods for determining qualitatively and quantitatively oil quality and degradation during frying.

(2) Description of Related Art

In the food industry and catering sector deep-frying involves using the same oil (oil is used herein to refer to edible oils, fats, shortenings and mixtures thereof) for several frying batches. This process results in serious chemical degradation of the oil involving oxidation, di- and oligo-polymer generation, hydrolysis and change in its physical properties. Among these changes, probably the most noticeable is that of viscosity which can even double during a prolonged frying process. The increase in viscosity reflects the generation of di- and oligo-polymers of triacylglycerols. It has been demonstrated that oil degradation due to frying has harmful effects on the human health. Health concern is becoming even more important if one takes into account the fact that consumption of fried foods out of home continues to increase. To prevent frying in oils unfit for human consumption and protect the consumers' health several countries have adopted recommendations and legal limits. According to those limits an oil or fat used for frying should be discarded and replaced by fresh when the total polymers have reached 12-15% per mass or the polar compounds 23-29% (depending on the country); other countries use viscosity as a criterion. It is, thus, important to detect the above thresholds in a reliable way in order to replace the oil as soon as it becomes necessary to do so.

In the case of food industry, determining the quality of an oil used for frying and complying with the above rejection limits is financially and technically feasible because quality control labs staffed with specialized personnel exist. There, the standard methods for quality determination of frying oils are performed as a part of routine analysis. Even if these methods are applicable in the food industry they are too much time consuming and they cannot be used for taking decisions during the frying process. On the other hand in the catering sector it is impossible to apply the above methods because apart from being time-consuming, they are expensive and require skilled personnel. As a result, in most restaurants, fast foods, canteens, sandwich places etc. (even in many of the most developed countries) no quality control measures are applied and fried foods can be of questionable quality and even could pose health concerns. In the larger catering units or fast-food chains, where HACCP (Hazard Analysis Critical Control Points) system is applied, the practice is to reject the oil after a few days of use. However, due to the multi-parameter aspect of frying where numerous variables come into play and affect oil degradation (oil composition, composition and quantity of foods being fried, time, temperature, contact with oxygen etc.) it is impossible to predict the level of oil degradation of an oil used for frying. As a consequence, it is impossible to establish adequate frying practices that prevent the use of a frying oil beyond its rejection limit while at the same time do not impose unnecessary oil rejection resulting to an undue increase of economic and environmental costs. From the above it is obvious that oil quality assassment is needed in order to decide when frying oil should be replaced by fresh one. The ideal frying oil quality determination method for both the food industry and the catering-restaurants-fast foods sector would be rapid, simple and reliable. In addition, for the catering sector such a method would also need to be safe for the foods being prepared at the same area and require no laboratory skill or laboratory equipment.

Several rapid tests that determine frying oil quality have been patented or published in scientific journals and some of them exist in the market as well. An independent review of those existing in the market has been recently published by Bansal G. et al. [Evaluation of commercially available rapid test kits for the determination of oil quality in deep-frying operations, Food Chemistry, 121(2010) 621-626]. Existing methods can be classified according to the compounds determined and/or according to the compounds reported by the methods results. According to this classification there are methods that determine:

a) free fatty acids via colorimetric reactions [U.S. Pat. No. 8,325,345; U.S. Pat. No. 4,654,309; FASafe™ (MP Biomedicals, USA), 3M™ Low Range Shortening Monitor (3M, USA)]

b) subgroups of oxidation products: carbonyl compounds via colorimetric reaction [Fritest® (Merck, Germany)], oxidized fatty acids via colorimetric reaction [Oxifrit-test® (Merck, Germany)], peroxides via colorimetric reaction (U.S. Pat. No. 5,670,374).

c) polar compounds via absorbance/colorimetric reaction [TPM very-Fry® (Test kit Technologies Inc. USA)], polar compounds via measurement of electrical properties [U.S. Pat. No. 6,469,521; U.S. Pat. No. 7,523,006; U.S. Pat. No. 7,834,646; U.S. Pat. No. 6,459,995; U.S. Pat. No. 6,436,713; U.S. Pat. No. 7,132,079; U.S. Pat. No. 7,390,666; World Patent WO 2012/036964 A2, World Patent WO 2011/022254 A2, World Patent WO 2010/148133 A1, Capsens 5000 (Center for Chemical Information Technology, Switzerland), FOM 310 (ebro Electronics, Germany), Testo 265 (Testo Inc., USA)], polar compounds via a thin layer chromatography principle (U.S. Pat. No. 7,390,666) polar compounds via measurement of viscosity [Viscofrit®, (Laboratorio de Seguridad Alimentaria S.L., Barcelona) Spain Patent ES 1043160)].

d) alkaline compounds via colorimetric reaction (U.S. Pat. No. 4,349,353)

e) color changes (South African Patent P/96/73728)

f) combined results and properties: polar and polymer compounds by dielectric constant and optical transmittance (U.S. Pat. No. 5,818,731), polar and polymer compounds by viscosity and density measurement (Fri-check®, World Patent WO 2000/71989 A1), free fatty acid and polar compounds content via optical absorption and fluorescence (U.S. Pat. No. 8,257,976).

In order for the said rapid tests to be suitable for assessing oil quality it is required that the group of compounds determined (or the property measured) represents adequately oil degradation during frying. It has been long established that free fatty acid concentration in an oil is not a reliable criterion for frying oil quality. The same holds for soap and peroxide concentration. In addition, measurement of oil color is completely unreliable since color is affected by numerous variables and not only oil chemical degradation.

A suitable method for rapid determination of oil quality should provide clear and unambiguous results. Results of methods involving colorimetric reactions can be problematic because the result of the method can be affected by the oil color. The oil color changes during frying and it depends on the oil type, food being fried and level of oil degradation. Furthermore, colors such as yellows, light reds, or light greens may be difficult to read. In addition comparison with a color scale can be subjective.

An appropriate method determining oil quality should determine only the property of the oil affected by oil degradation and not a property affected by other compounds or other external variables. Many of the proposed methods determine electrical properties of oil. It is true that chemical reactions occurring in an oil during frying affect its electrical properties. However, methods determining electrical properties have a serious drawback: the electrical properties of oils are also highly affected by the food moisture retained in the oil; they are also affected by the presence of food particles in the oil. Such effects can induce significant deviations of actual oil degradation. In addition, attachment of solid residues or water droplets (e.g. after cleaning) on the sensor can result in an erroneous measurement.

A certain category of oils "virgin oils" produced only with physical processing have a higher concentration in polar compounds compared to the rest. These polar compounds are not the result of oil quality degradation; they are present in the raw material and are not removed during the mild physical processes used for their extraction. Moreover, in some cases compounds having higher polarity than the oil (e.g. polyphenols in virgin and extra virgin olive oil) are indices of higher than lower oil quality. Therefore in such cases the determination of polar compounds would unduly overestimate degradation.

Regarding the safety of proposed methods, many of them cannot be used close to food preparation areas since they use unsafe, corrosive or explosive chemicals (e.g. Oxifritest®, Fritest®). Furthermore in some of the methods, such as some of those measuring electrical properties, where the probe is inserted directly in the fryer and not replaced after each measurement there are concerns about the effective cleaning of the measuring probe in respect to food safety.

Regarding the simplicity of above tests some of these tests require laboratory skill (FASafe™, TPM Veri-fry®), some require laboratory equipment (TPM Veri-fry®) or require scientific background (Viscofrit®). Therefore it is difficult to use these tests in fast-foods, restaurants or catering units which lack either technical or scientific personnel or laboratory equipment.

What is however most significant regarding rapid tests existing in the market is that in most cases they do not provide accurate results as shown in an independent review (Bansal et al., 2010). Some tests highly overestimate (FASafe™) or highly under estimate results (Oxifrit-Test®). In other tests high differences with standard methods have been found (3M™ Low Range Shortening Monitor). Finally, all methods based on the measurement of electrical properties examined by Bansal et al. (2010) (i.e. Capsens 5000, FOM 310, Testo 265) provide non-satisfactory results for all food/oil combinations.

The above review on existing methods shows that although a lot of rapid methods have been proposed to meet the need of rapid assessment of frying oil quality all above methods present serious drawbacks related to the principle of the method, the reliability and accuracy of results, the safety for use in food preparation/processing areas and the simplicity to use by personnel lacking laboratory skill.

The above review shows also that the principle of viscosity changes has been far less exploited up to date for the development of fast methods, although the di- and oligopolymers of triacylglycerols constitute the newly formed compounds with higher concentration in an oil close to rejection limit. In addition, it has been shown that the di- and oligopolymers of triacylglycerols formed during frying correlate perfectly with the increase oil's viscosity [Kalogianni E. et al., Effect of repeated frying on the viscosity, density and dynamic interfacial tension of palm and olive oil, Journal of Food Engineering 105 (2011) 169-179]. Furthermore, good correlations have been found between the total polymer compounds and polymer compounds and viscosity. Another aspect that should not be disregarded is that oil viscosity has been also related to oil uptake.

To the applicants knowledge the first who exploited the measurement of viscosity in order to assess frying oil quality are Kress-Rogers E. et al. [Development and evaluation of a novel sensor for the in situ assessment of frying oil quality, Food Control, July 1990, 163-178] who adapted a viscosity probe from GEC Marconi Ltd. and developed an in-situ probe for deep-fryers. The method measures the dampening and resonance frequency of vibration of two short vibrating steel tubes excited by piezocrystals. The test is safe and according to the authors the test showed good correlation with several parameters regarding oil degradation, however no independent report has been found on this method. A similar ultrasonic rapid method for viscosity determination in liquids is presented in U.S. Pat. No. 4,721,874. However, this method as presented is not especially adapted for frying oil quality assessment.

Another rapid test based on the change in viscosity principle is the Viscosfrit® test (Laboratorio de Securidad Alimentaria S.L. Barcelona, Spain). The test is simple and safe. It measures the time required to empty a standard funnel-like cone filled with the oil in question. The cone is emptied by gravity through a small calibrated hole at the bottom. The time measured is compared with a table of values in order to decide whether the oil should be discarded or not. The drawback of this test is that the user should know whether monounsaturated or polyunsaturated fatty acids prevail in the oil composition. Therefore, users with lack of food chemistry knowledge such as people working in restaurants have difficulty in using the test.

Finally, the third test based on viscosity (and density) measurement is Fricheck® (World Patent WO 2000/71989 A1). In this test the time required for a piston-like body dropped in a tube containing the oil at 50° C. is related to the viscosity and density of the fluid. The test provides combined results on polymer and polar material. Limited independent research exists on this test reporting that results of this test are very tolerant.

Washburn and Lukas [Washburn E. W., The dynamics of capillary flow, Physical Review, 17 (1921) 273-283] were the first to analyze the rate of liquid penetration in a horizontal tube of capillary dimension. Other researchers studied capillary penetration (or wicking) in capillary tubes as well as in porous systems with pores of capillary dimensions. In these works, the effects of gravity, pore size distribution, inertia effects etc. were examined [van Oss C. J. et al., Determination of contact angles and pore sizes of porous media by column and thin layer wicking, Journal of Adhesion Science and Technology, 6 (1992) 413-428; Marmur A. amd Cohen R. D., Characterization of porous media by the kinetics of liquid penetration: The vertical capillaries model. Journal of Colloid and Interface Science, 189(1997), 299-304; Siebold A. et al., Effect of dynamic contact angle on capillary rise phenomena, Colloids and Surfaces A: Physicochemical and Engineering Aspects, 161 (2000) 81-87; Marmur A., Kinetics of penetration into uniform porous media: testing the equivalent-capillary concept, Langmuir, 19 (2003) 5956-5959]. Scientific knowledge on capillary penetration has been used in the past in order to determine contact angles and pore sizes in porous media and powders (van Oss et al., 1992). To the applicants knowledge no one has used in the prior art the measurement of the rate of capillary penetration in order to determine the viscosity and/or surface tension of a liquid and in particular frying oil quality.

BRIEF SUMMARY OF THE INVENTION

The present method determines the viscosity, surface tension and/or surface tension/viscosity ratio of a liquid via the measurement of the rate of spontaneous penetration of the liquid into a test medium due to capillary phenomena.

In one aspect of the invention the liquid sample is edible oil. The term oil as used herein includes oils, fats, shortenings and mixtures thereof. The oils can be synthetic or naturally occurring. The oils can be virgin, issuing from a solvent extraction process or refined. Where the oil is solid at room temperature the oil can be heated in a temperature higher than its melting point.

In one aspect of the invention the method can be used in order to determine qualitatively and quantitatively the degree of oil degradation during heating, frying or other processing method involving high temperatures or inducing changes in viscosity and/or surface tension such as the generation of polymer compounds, formation of polar compounds or scission products. In a specific implementation of the method it can be used to assess the rejection point or replacement of frying oils used in industrial, catering or domestic fryers.

The present invention relates the said liquid property(ies) to the rate of spontaneous liquid penetration in a test medium due to capillary phenomena. The selection of test medium is critical for the method. Preferably, control or measurement of the liquid temperature is required. From the capillary penetration data and using appropriate equations the viscosity (or viscosity/surface tension ratio) is calculated. In addition, any other property correlated to viscosity can be calculated as well (e.g. concentration in polymer and/or polar compounds in frying oils). Preferably, calculations are performed automatically by the apparatus and the user can be informed on the results on a display.

This invention provides a rapid and inexpensive means for the determination of liquid properties and in one specific implementation provides qualitative and quantitative determination of degradation compounds formed during frying and assessment of frying oil quality. In the said specific implementation it can be used to rapidly determine the rejection/replacement point of frying oils. The property measured correlates to a major group of compounds formed during the frying and/or heating process and represents well oil degradation during frying. The proposed device is easy to operate even for users lacking laboratory skill and in areas where laboratory equipment is unavailable. The technique requires only a small oil sample (typically a few mL). Furthermore, it is safe to use in food processing or food preparation areas since no harmful, corrosive, explosive or other unsafe chemicals are used because it can be constructed by safe material. The method results can be produced rapidly (within a few seconds up to a few minutes) and are clear and unambiguous for the user to read. The assessment of oil quality does not require the user to have any scientific background.

DETAILED DESCRIPTION OF THE INVENTION

The present method determines the viscosity, the surface tension and/or the surface tension/viscosity ratio of a liquid via the measurement of the rate of spontaneous penetration of the liquid into a test medium due to capillary phenomena. Exemplary test media include, but are not limited to, porous media having pore sizes of capillary dimensions, a tube or set of tubes (straight or not) of capillary dimensions, a packed bed of particles forming pores of capillary dimensions. It is contemplated that any medium having pores of capillary dimensions where spontaneous penetration of the liquid occurs can be used as the test medium.

In one aspect of the invention the liquid sample is edible oil. The term oil as used herein includes oils, fats, shortenings and mixtures thereof. The oils can be virgin, issuing from a solvent extraction process or refined. The oils can be synthetic or naturally occurring. Where the oil is solid at room temperature the oil can be heated in a temperature higher than its melting point.

In one aspect of the invention the method can be used in order to determine qualitatively and quantitatively the degree of oil degradation during heating, frying or other processing method involving high temperatures or inducing changes in viscosity and/or surface tension such as the generation of polymer compounds, polar compounds formation or scission products. In a specific implementation of the method it can be used in order to assess the rejection point or replacement of frying oils used in industrial, catering or home fryers.

It will be readily understood by those skilled in the art and science that the components and procedure of the present invention as generally described and illustrated in the Figures herein and accompanying text, could be arranged and designed in a wide variety of different configurations while still utilizing the inventive concept. Thus the following more detailed description of the preferred embodiments of the system and method of the present invention, as presented in FIGS. 1 and 2 and accompanying text is not intended to limit the scope of invention but is merely representative of the presently preferred embodiments of the invention.

Figure 1:
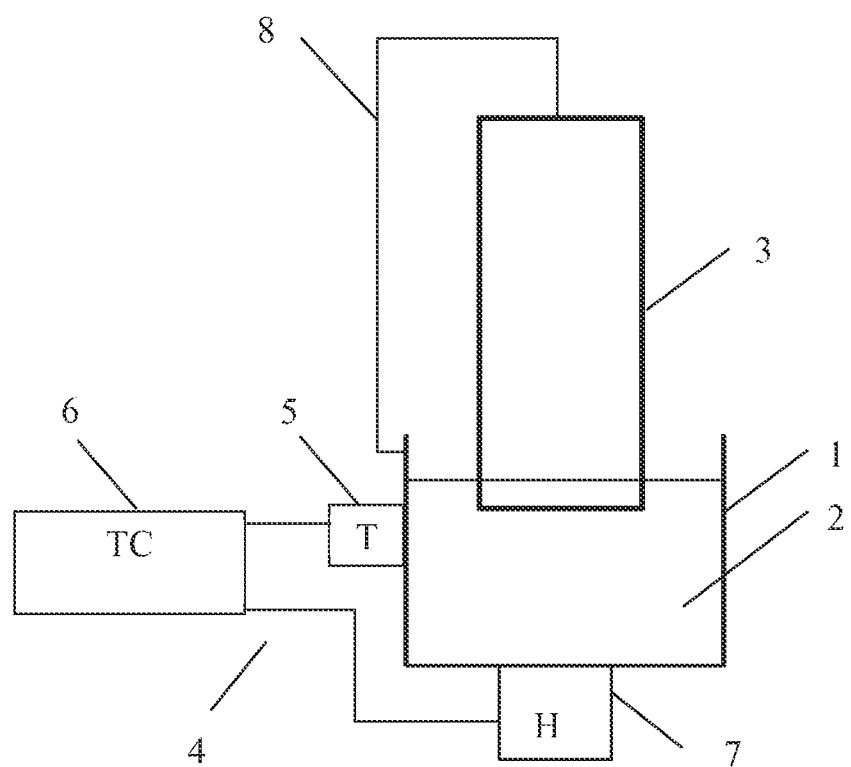
FIG. 1. Schematic diagram of a preferred embodiment of the apparatus embodying the present invention. It consists of a liquid container 1 for receiving the sample 2, a test medium 3, means 4 for measuring and/or changing the temperature of the sample, such as a temperature probe 5, temperature controller 6 and a heater 7. It also comprises a system for holding and/or setting/controlling the position of the porous medium 8.

A preferred embodiment of the apparatus of the present invention is schematically illustrated in FIG. 1. The construction of this embodiment lends itself to usage both in a laboratory as well in the place where food is processed, cooked or prepared (e.g. kitchen, food industry, catering unit) because it can be constructed by safe material and involves no harmful substances for foods being prepared. The present invention lends its self to usage not only in the food industry but also in other industries where examination of viscosity or/and surface tension changes in a liquid is required.

In case both the viscosity ($\eta$) and the surface tension ($\gamma$) considerably change during the degradation process the method determines both properties as a ratio (i.e. $\gamma/\eta$). However, if during the degradation process one of the said properties does not change significantly, the method can determine the other property. By means of example if the surface tension of the liquid does not change considerably during the degradation process then the method can be used in order to determine liquid viscosity.

The apparatus depicted in FIG. 1 includes: a liquid container 1 for receiving the sample 2, it also includes a test medium 3. The FIG. 1 embodiment further comprises means 4 for measuring and/or changing the temperature of the sample, such as a temperature probe 5, temperature controller 6 and a heater 7. Finally, the FIG. 1 embodiment comprises a system for holding and setting/controlling the position of the porous medium 8.

The test medium 3 can be, but is not limited to, a porous medium having pore sizes of capillary dimensions. It is however contemplated that any medium having pore(s) or tube(s) in the said size can be used instead of a porous medium. By way of example, other possible test media 3 include a tube or set of tubes (straight or not) of capillary dimensions, a packed bed of particles forming pores of capillary dimensions etc. The size and shape of the test medium can vary. The material of the test medium described as said should be such that capillary penetration occurs spontaneously. By means of example the apparatus depicted in FIG. 1 includes a porous strip as a test medium. By means of example the porous medium is positioned vertically in FIG. 1. Nevertheless, the porous medium could be positioned horizontally or in any other direction as long as one could put a part of test medium in contact with the liquid under test. By means of example in FIG. 1, the test medium has been in part inserted in the liquid under examination. Nevertheless, in another embodiment the liquid could come into contact and fed to the test medium by other possible means (e.g. syringe, piston or tube on the top or sides of a test medium).

The liquid container 1 should be capable of containing a sample quantity no less than the quantity required to saturate the test medium 3. By means of example the liquid container has been placed under the test medium. Preferably, in the said position of the container 1, the shape and size of the container, should be such that after liquid penetration in the test medium the liquid level in the container does not drop significantly. By means of example only a few mL of oil would be enough.

The FIG. 1 embodiment further comprises means 4 for changing and/or measuring the temperature of the liquid sample. The means 4 can be implemented by any suitable means. Examples include a heat resistance or a heat tape, a liquid bath or sand bath; however other suitable means where operating in response to electricity, combustion or other chemical reaction otherwise can be used. For purposes of illustration the means 4 depicted in FIG. 1 includes a heat resistance 7 connected to a liquid container. Also by means of example a temperature probe 5 and a temperature controller 6 are used to measure and control the sample temperature. Preferably, means informing the user that the sample has reached the desired temperature is required. Alternatively to informing the user the apparatus can have means to automatically start the measurement at the desired temperature. Although the apparatus depicted in FIG. 1 includes means 4 for controlling the temperature of the sample the temperature controlling system could be replaced by a temperature measurement system that notifies the user (e.g. by an auditory or optical or any other signal) that the sample is in the desired temperature (range). In that case the liquid needs to be added in the container in a temperature higher than the one defined for the measurement (e.g. sample added in frying temperature and measured at 50° C.). In another possible example, the temperature controlling/measuring system may not be present in the apparatus at all, and measurements are performed at ambient temperature provided that this temperature is relatively stable and the sample is liquid in ambient conditions. Finally, in another possible example the temperature could be different in different measurements. In this latter example measurement of the temperature should be used to subsequently account for temperature effects and correct the results with appropriate equations.

Finally, the FIG. 1 embodiment comprises a system 8 for holding and setting/controlling the position of the porous medium. This system could be implemented by any possible device (e.g. consisting of mechanical and electronic parts; a manual or automatic device) serving the scope of bringing and holding the test medium in contact with the test liquid.

In order to perform measurements using the embodiment displayed in FIG. 1 it would be required to have means of measuring the rate of liquid penetration (not shown in FIG. 1). This can be done, but is not limited to, by measuring the distance (h) or area (A) the liquid has penetrated the test medium and the time (t) required to do so. This can also be done by measuring the weight (w) or volume (v) of the liquid taken up by the test medium as a function of time or by any other possible means. It is contemplated that the said measurement(s) of liquid penetration rate can be performed by any possible means.

If the liquid penetrates spontaneously in the test medium [i.e. the contact angle ($\theta$) between the test medium and the liquid is <90°] the liquid penetration rate is a function (f) of the liquid and material properties:

$$R = f(r, \cos\theta, \gamma, \eta) \quad (1)$$

R can be expressed as follows:

$$R = h^2/t = \beta A/t = \beta' w^2/t = \beta'' v^2/t \tag{2}$$

Where $\beta$, $\beta'$, $\beta''$ are constants. In Equation (1) r is the capillary radius for a straight capillary pore (e.g. in the case of a test medium consisting of one straight pore). In any other case (e.g. in case of the porous medium characterized by more than one pores having different sizes and shapes) r represents the effective pore radius of the medium $r_{eff}$. $r_{eff}$ can be determined by wicking tests. This is a known procedure to those skilled in the art and science. In Equation (1) $\theta$, $\gamma$ and $\eta$ have been defined previously.

In the case where some basic conditions hold ($\theta$ is <90°, the effect of gravity on liquid penetration is absent or negligible, the flow in the capillary or capillaries is laminar, the liquid meniscus is hemispherical and an adsorbed film of the penetrating liquid preexists or forms previous to liquid penetration) Equation (1) takes the form:

$$R = r \cdot \cos\theta \cdot \gamma / 2\eta \tag{3}$$

Given the range of liquid properties expected, and namely the expected variation of $\gamma$ and $\eta$ within samples (e.g. in fresh, fried, heated and oxidized oils) one can appropriately select the properties of the test medium so as to:

a) $\cos\theta$ to be unaffected by R
b) R to be unaffected by the spreading pressure
c) $\cos\theta$ to be close or equal to unity
d) $\cos\theta$ to be independent of the position of the liquid inside the material
e) $\cos\theta$ and r to be unaffected by ambient humidity
f) r to be constant or the pore network characteristics to be uniform along the test medium
g) the effect of gravity on R to be absent or negligible
h) laminar flow to prevail in the pores The selection of the test medium according to the above criteria can be obvious to those skilled in the art and science and can be verified by appropriate tests.

In case all above conditions are respected and for a given porous medium Eq. (3) takes the form:

$$R = \alpha \gamma / \eta \tag{4}$$

where $\alpha = r\cos\theta/2$ and $\alpha$ is constant. Therefore R is linearly dependent on $\gamma/\eta$.

In the case one or more of the above conditions do not hold corrections in equations (3) and (4) would be required. These corrections are easy to define by performing tests with the liquids and test medium in question and measuring the liquid penetration rate.

The results of $\eta$ or $\gamma/\eta$ obtained by the said method can be correlated with polymer and polar compounds in order to obtain equations or data matrices. The said equations or data matrices can then be used to convert the method measurements to the desired oil property. The above determinations, correlations and procedures for making equations and data matrices are obvious to those skilled in the art and science.

Figure 2:
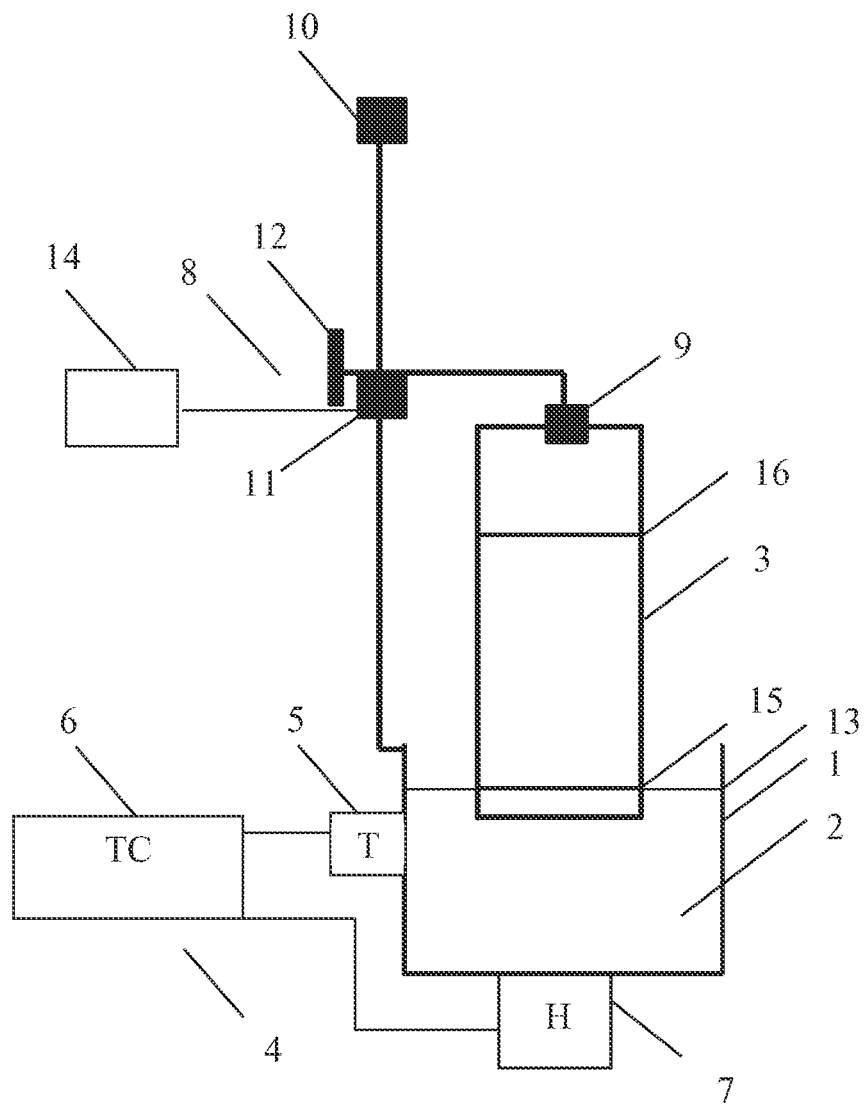
FIG. 2 Schematic diagram of a specific implementation of another preferred embodiment similar to the one illustrated in FIG. 1. Portions of the specific implementation shown in this Figure corresponding to Portions identified in FIG. 1 are indicated by like reference numerals. In addition to portions defined by numerals 1 to 8 in the description of FIG. 1, this Figure comprises: a holder 9 holding the test medium, an upper stop (terminal) 10 and lower stop 11, means 12 used to move the sample holder and sample between stops 10 and 11. 13 denotes the liquid level in the container. The present Figure also comprises unit 14 consisting of at least a timer, an on-off button and a system notifying the user about the results of the measurement. 15 and 16 are the upper and lower marks on the test medium defining the beginning and end of liquid penetration time and the penetration distance.

A specific implementation of the embodiment shown in FIG. 1 is schematically illustrated in FIG. 2. Portions of the specific implementation shown in FIG. 2 corresponding to Portions identified in FIG. 1 are indicated by like reference numerals. The test medium 3 in the specific implementation illustrated in FIG. 2 is a porous medium in the form of strip. It is made from material that has a contact angle with the liquid under test lower than 90°. Preferably, a non-hygroscopic or moisture absorbing material should be used. Preferably the test medium does not react with the liquid under examination and consequently the properties of the liquid and the test medium preferably remain unaffected by liquid penetration. Preferably the test medium is disposable. The length of the strip would be preferably 1 to a few cm. Preferably the effective pore radius of the test medium would be such that liquid penetration is completed within a few seconds up to a few minutes. Preferably the distribution of pore sizes would be as narrow as possible and the distribution of pore sizes, tortuosity and pore interconnectivity should be uniform along the material. In the specific implementation illustrated in FIG. 2 the penetration distance should be known in order to measure the penetration time. For that reason and by means of example the test medium has two horizontal marks on it: marks 15 and 16 and the distance between the said marks is known. Also by means of example mark 15 coincides with the liquid level 13. Nevertheless, mark 15 could be placed in any other position between the liquid level and mark 16, provided that the two marks define the beginning and the end of measurement of liquid penetration length and time. Preferably, and in the case marks 15 and 16 are used the test medium should have also a mark (e.g. an arrow) to inform the user on which direction should be used.

The holding and position setting/controlling system 8 in FIG. 2 is comprised by a holder 9 holding the porous medium in vertical position. Preferably, the level of the holder (and therefore the level of the porous medium) can be changed and secured with the aid of any appropriate means (e.g. automatically or using a knob) upwards and downwards in the vertical bar between an upper and lower position. By means of example the said positions defined by the upper stop 10 (optional) and lower stop 11. The holder is moved or to a position higher than the lower stop 11 (or if present to the upper stop 10) in order to add the test medium in the system without putting it into contact with the liquid before the measurement. The porous medium is lowered to the lower stop 11 with the aid of the holder 9 to start the measurement. Preferably, the lower stop 11 has a trigger on it such as by means of example a button, a sensor, electrical circuit or any other means that can be used as trigger to activate the timer in unit 14. The aim of the trigger is to activate the timer once the porous medium has come into contact with the liquid. Instead of a trigger the user could press a start button added in unit 14, to start the measurement.

The specific implementation of the embodiment illustrated in FIG. 2 comprises also a unit 14 consisting of at least a timer, an on-off button and a system notifying the user about the results of the method. The latter said system could be implemented by any possible means. Preferably, and depending on the type of data intended to be displayed to the user, a data logger-processor is also included in unit 14. By means of example, the data logger-processor can be used to store measurements, make calculations and provide information to the user interface/display. In another implementation unit 14 can be absent and timing can be performed independently. The information displayed to the user could, by means of example, be a numerical value indicating the viscosity, viscosity/surface tension ratio, the concentration of polymer compounds, the concentration of polar compounds, a combined value issuing from both polar and polymer compounds concentration. The indication could also have the form of a graph, a point in a graph or a table. Alternatively, the indication could also be a parameter or a signal that while not directly equal to a numerical value it is associated with a value and can serve to allow the user to ascertain the quality of the oil or ascertain whether the oil is still suitable for use. The results of the method could also be communicated to a personal computer, laptop or any other portable electronic device with appropriate hardware and software.

In the specific implementation of the embodiment illustrated in FIG. 2 it is contemplated that the time interval Δt required for the liquid to penetrate the test medium from mark 15 to mark 16 is measured. Therefore the presence or passage of the liquid under test from these positions should be detected. Detection can be performed by any possible means. By means of example, the user could visually detect the position of the penetration front and communicate it to unit 14. This requires the appropriate selection of the porous medium. By means of example, a transparent, semi-transparent or light colored test medium is required. In the case of transparent or light colored oils the visual detection of the liquid penetration front could be aided by adding the appropriate dye or colorant in the liquid (e.g. an oil soluble colorant in oil). Preferably a food grade colorant (e.g. annatto or beta carotene) should be used for that purpose.

In the specific implementation of the embodiment illustrated in FIG. 2 the oil sample 2 is added in the container 1 to a preferably predefined level 13. By way of example possible means for adding a defined oil quantity in the container having a mark in the container to inform the user of the liquid level, use an oil sampler with a predefined volume, to weigh or measure the sample volume prior to addition in the container.

The FIG. 2 embodiment preferably further comprises means 4 for measuring and or changing the temperature of the sample. By means of example, means 4 include a heater, a temperature probe 5 and a temperature controller 6. Means 4 also comprises means for notifying the user that the liquid is in the desired temperature.

In the case of the specific implementation of the embodiment illustrated in FIG. 2 and explained as said, given Equation (4) and given the distance from mark 15 to mark 16 ($h_{15-16}$) it follows that:

$$t_{15-16} = \alpha' \eta / \gamma \quad (5)$$

where $t_{14-15}$ is the time required for the liquid to penetrate the porous medium from mark 15 to mark 16 and $\alpha' = (1/\alpha) h_{15-16}^2$. Where $\alpha$ is as defined in Equation (4).

An example of possible operation using the apparatus illustrated in FIG. 2 is briefly described as follows: a) The temperature control/measurement system 4 is set on. b) The sample 2 is added in the container 1 and left there in order to obtain the measurement temperature. c) The user adds the test medium 3 in the holder 9 (holder position to upper stop 10) d) Once the liquid has attained the desired temperature the test medium 3 is lowered in the liquid with the aid of the holder 9 (holder position to lower stop 11) and the timer is set (automatically or by the user). e) The timer is set off once the liquid front has reached mark 16. f) The instrument, after appropriate calculation or comparison with a data matrix, notifies the user on the degree of sample degradation.

Regarding the application of the above method and apparatus as depicted in FIG. 2 and for the case of frying oils the following can be useful for calculations and determination of oil degradation: Both $\eta$ and $\gamma$ change during frying: $\eta$ due to the generation of di- and oligo-polymers of triacylglycerols and $\gamma$ due to the formation of compounds more polar than the oil. Nevertheless, $\eta$ is significantly affected by frying (up to 100% or more) whereas $\gamma$ only a little (in general less than 5 or 10%). Therefore, the results of the said method are expected to reflect chiefly changes in viscosity and the generation of di- and oligopolymers in oils used for frying, cooking or heating.

In fact the viscosity ($\eta_f$) of an oil subject to frying, to high temperature or excessive oxidation is a function of its viscosity when fresh ($\eta_o$) and the concentration of polymer compounds ($C_{pol}$). With a good approximation one could write:

$$\eta_f = \eta_o + dC_{pol} \quad (5)$$

Generally, for oils up to their rejection limit a constant can be used for d with good approximation. It is contemplated however that d can be replaced also by any non-constant term if necessary.

Preferably, for an accurate determination of $C_{pol}$ the determination of liquid properties of the oil in an unused (or fresh) condition would be required. In this case a good approximation of polymers formed in the sample considering negligible surface tension effects on the wicking rate would be:

$$\Delta t_{15-16} = \alpha'' \Delta C_{pol} \quad (6)$$

Where $\Delta t_{15-16}$ the difference in time required for the fresh and degraded liquid to penetrate between marks 15 and 16, $\alpha'' = \alpha' d / \gamma$, $\gamma$ a constant representative surface tension value for oils and $\Delta C_{pol}$ the concentration of polymers generated during the degradation (e.g. frying) process.

Alternatively, and depending on the desired accuracy of the method one could skip the step of measurement with fresh oil and measure only the degraded one. This can be made possible because the difference in viscosity between different oil types is smaller than the increase in viscosity of those at the rejection limit. In this case:

$$t_{15-16} = f(C_{pol}) \quad (7)$$

By way of example the use of the embodiment depicted in FIG. 2 could allow the user to select between the two modes of use (with or without measurement of the fresh oil) whether greater simplicity or greater accuracy is required.

It should finally be added that the increase in viscosity correlates also with the concentration of total polar material generated in an oil during frying ($\Delta C_{TPM}$). Consequently:

$$\Delta t_{15-16} = f(\Delta C_{TPM}) \quad (8)$$

The said relations between $t_{15-16}$ or $\Delta t_{15-16}$ with $C_{pol}$, $\Delta C_{pol}$ or $\Delta C_{TPM}$ are easy to establish for those skilled in the art and science.

In the case of specific implementation and described as said the apparatus measures the time ($t_{15-16}$) required for the liquid to penetrate a given distance ($h_{15-16}$). It is contemplated however that the measurement can be also performed by measuring the penetration distance ($h_{15-16}$) for a given penetration time ($t_{15-16}$). In a simplified version of this latter implementation mark 16 could be used as the limit for frying oil rejection. In this case $h_{15-16}$ is defined as the distance penetrated by an oil at the rejection limit for a given penetration time. If for that same given penetration time an oil sample penetrates beyond mark 16 then the oil is still usable. If, on the other hand, for the same given penetration time an oil sample does not reach mark 16 than the oil should be replaced by fresh. In the case of this simplified version of the latter implementation unit 14 in FIG. 2 would need to include only a timer.

EXAMPLE 1

Test determining the penetration time of oils with the said method and correlation of that time to total polymer compounds Samples were tested using the methods of this invention and an apparatus similar to the one depicted in FIGS. 1 and 2.

Oil samples: Sunflower oil (polyunsaturated fatty acids prevail in its composition) and virgin olive oil (monounsaturated fatty acids prevail in its composition) were used. The oils were heated frying temperatures (170° C.) for 7 days and for 4 hours each day. Samples were taken from the fresh oils (i.e. as purchased) and at several time intervals during the above heating process.

Measurement of polymer compounds: The concentration of polymer compounds (di- and oligopolymers of triacyglycerols: $C_{pol}$) in the samples was determined using HPSEC (High Pressure Size Exclusion Chromatography) following the method by Wolff J. P. et al. [Determination of polymerized triglycerides in oils and fats by high performance liquid chromatography: results of a collaborative study and the standardized method, Pure and Applied Chemistry, 63(1991), 1163-1171]. A stainless steel 300 mm×7.5 mm i.d., PL-gel 100 A ° (polystyrene-divinylbenzene co-polymer in toluene) column with 5-μm packing (Polymer Laboratories Ltd.), connected to a PL-gel guard column (Polymer Laboratories Ltd.) was used for the analysis.

An apparatus was prepared in accordance to FIGS. 1 and 2. A polyethylene porous medium was used as a test medium (POREX®, Porex Technologies GmbH, Aachen; $r_{eff}$=13.7 μm). Preliminary experiments verified linear response between $h^2$ and penetration time. The apparatus lacked temperature control but included temperature measurement. A penetration length of 1.5 cm was selected for the measurements. It was not necessary to dye the oils prior to measurement: the light color and low thickness of the porous material allowed for visual determination of the wicking front. The penetration time ($t_{15-16}$) required for each of the oils to penetrate the said distance in the porous sample was measured using a stopwatch. Measurements were taken in ambient temperatures which varied between 27 and 31° C.

Figure 3:
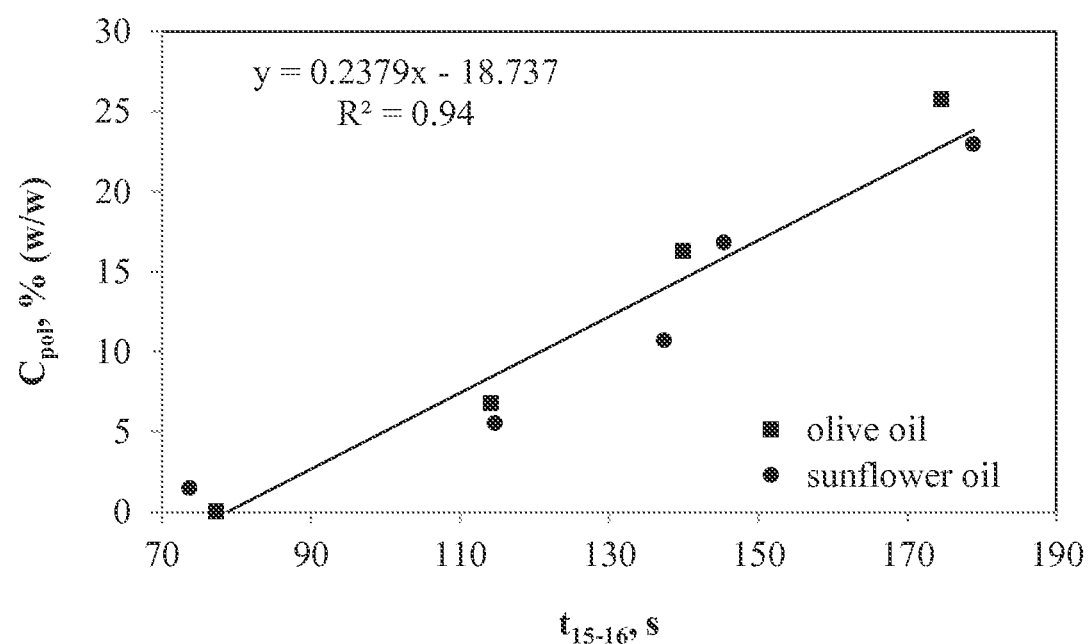
FIG. 3 Correlation of weight (w/w) percentage of polymers ($C_{pol}$) in sunflower and virgin olive oil samples with penetration time $t_{15-16}$ for a penetration height of 1.5 cm in a polyethylene porous medium having $r_{eff}$=13.7 μm. Where R is the coefficient of determination of the data points to the line. The equation corresponds to the correlation equation between $C_{pol}$ and $t_{15-16}$.

FIG. 3 displays the results of penetration time plotted against the polymer concentration of the oils. It is shown that despite the differences in temperature between measurements a good correlation was found between $C_{pol}$ and $t_{15-16}$. The results indicate that one could predetermine $t_{15-16}$ value knowing $C_{pol}$ and similarly knowing the $t_{15-16}$ in the oil permits the determination of $C_{pol}$. Furthermore, the penetration time for a fresh oil (79 s) is significantly different compared to this of an oil at the rejection limit ($C_{pol}$=15%: 142 s). According to the results in FIG. 3 an oil should be discarded when $t_{15-16}$ exceeds 142 s.

It will be appreciated by those skilled in the art and science that while the invention has been described above in connection with particular embodiments and an example the invention is not necessarily limited to the said embodiments and example and that numerous other embodiments, examples, uses, modification and departures from the embodiments, examples and uses may be made without departing from the inventive scope of this application.

What is claimed is:

1. A method for determining a quality attribute of a liquid including oils, frying oils, edible oils, fats, shortenings and mixtures thereof via the measurement of the rate of penetration of said liquid into a test medium comprising the steps of:
   (a) providing a test medium that has such properties that cause spontaneous penetration of the liquid under examination when in contact with said liquid;
   (b) contacting a portion of the test medium with the liquid under examination;
   (c) allowing enough time for the liquid to penetrate the test medium;
   (d) measuring the rate of liquid penetration; and
   (e) using the measurement of penetration rate in order to determine a quality attribute of the liquid.

2. The method of claim 1 wherein the means of measuring the rate of penetration is selected from the group of measuring the penetration distance as a function of time, penetration square distance as a function of time, penetration distance for a given penetration time, penetration square distance for a given penetration time, penetration time for a given penetration distance, penetration area as a function of time, penetration area for a given penetration time, penetration time for a given penetration area, penetration weight as a function of time, penetration weight for a given penetration time, penetration time for a given penetration weight, penetration volume as a function of time, penetration volume for a given penetration time and penetration time for a given penetration volume.

3. The method of claim 1 wherein the measurement penetration rate is used as an input to equations or correlation algorithm in order to determine a liquid quality attribute selected from the group of viscosity, viscosity to surface tension ratio, surface tension, frying oil quality, frying oil quality deterioration level with respect to regulations and recommendations by authorities for frying oil use and replacement, frying oil discarding time, polymer compound concentration in an oil, total polar compound concentration in an oil, combined quality characteristic including polar and polymer compound concentration in an oil, oil quality, oil discarding time, increase in polymer compounds in an oil, and increase in polar compounds in an oil.

4. The method of claim 3 wherein the calculated values of liquid quality attribute are compared to a predefined value or table of values in order to provide an overall quality assessment for the liquid under examination.

5. A system for measuring a quality attribute of a liquid including oils, frying oils, edible oils, fats, shortenings and mixtures thereof comprising:
   (a) a test medium that has such properties that cause spontaneous penetration of the liquid under examination when in contact with said liquid;
   (b) a liquid container for receiving the sample;
   (c) means for measuring and/or controlling the temperature of said liquid;
   (d) means for holding the test medium, setting the position of the test medium and putting a portion of said test medium into contact with the liquid under examination when the liquid is at the desired temperature so that the liquid will penetrate the test medium;
   (e) means for measuring the rate of liquid penetration; and
   (f) means for using the measurement of penetration rate in order to determine a quality attribute of the liquid.

6. The system as recited in claim 5 wherein the test medium is selected from the group of porous medium having pores of capillary dimensions, packed bed of particles having pores of capillary dimensions, tube having internal diameter of capillary dimensions, set of tubes having internal diameters of capillary dimensions; and wherein the test medium presents a contact angle with the liquid under examination of below ninety degrees.

7. The system as recited in claim 5 wherein the test medium is a porous medium having pores of capillary dimensions and narrow size distribution; wherein the distribution of pore sizes, tortuosity and pore interconnectivity is uniform along the material; and wherein the porous medium presents a contact angle with the liquid under examination of below ninety degrees.

8. The system as recited in claim 5 wherein the test medium is a light colored porous strip.

9. The system as recited in claim 5 wherein the test medium has such a combination of effective pore radius and contact angle with the liquid that the measurement is completed within a few seconds up to a few minutes.

10. The system as recited in claim 5 wherein the test medium properties are not affected by ambient humidity, the test medium does not react with the penetrating liquid and wherein the test medium and penetrating liquid properties are not affected by liquid penetration.

11. The system as recited in claim 5 wherein the test medium is selected from the group consisting of glass, polymeric material, cloth and paper.

12. The system as recited in claim 5 wherein the test medium is made of polyethylene.

13. The system as recited in claim 5 further comprising a colorant which is soluble to the liquid under examination; wherein the colorant is added to the liquid prior to its penetration to the test medium and aims at facilitating the detection of the penetration front.

14. The system as recited in claim 5 further comprising a colorant which is soluble to the liquid under examination; wherein the colorant is a food-grade colorant including beta-carotene and annatto; and wherein said colorant is added to the liquid prior to its penetration to the test medium in order to aid the detection of the penetration front.

15. The system as recited in claim 5 wherein the means determining the rate of penetration involve visual detection of the position of the penetration front or the amount of penetrated liquid.

16. The system as recited in claim 5 wherein the means of determining the rate of penetration involve detection of the position of penetration front by a sensor.

17. The system as recited in claim 5 wherein the means of determining the rate of penetration involve detection of the position of penetration front using a balance.

18. The system as recited in claim 5 wherein the liquid container contains sample quantity no less than the quantity required to saturate the test medium.

19. The system as recited in claim 5 wherein the test medium lower portion is put in contact with the upper portion of the test liquid in the liquid container; and wherein the shape and size of the liquid container are such that after liquid penetration the liquid level does not drop significantly.

20. The system as recited in claim 5 wherein the test medium lower portion is put in contact with the upper portion of the test liquid in the liquid container; wherein the test medium has at least two marks on it, first said mark indicating the beginning and second said mark the end of penetration so that the time required for the liquid to penetrate from first said mark to second said mark is measured.

21. The system as recited in claim 5 further comprising means for measuring the time required for the liquid to travel between two predefined positions in the test medium in order to determine the rate of liquid penetration and said time is communicated to the user.

22. The system as recited in claim 5 further comprising means for measuring the time required for the liquid to travel between two predefined positions in the test medium; wherein the system further comprises means for communicating the measured time to a microprocessor connected to the apparatus, said microprocessor stores measured time, uses said time for calculations of a liquid quality attribute and provides an output indicative of the quality of the liquid.

23. The system as recited in claim 5 further comprising means for measuring the time required for the liquid to travel between two predefined positions in the test medium; wherein the system further comprises means for communicating the measured time to a microprocessor connected to the system, said microprocessor stores measured time, uses said time to calculate the liquid viscosity, viscosity to surface tension ratio or surface tension and provides an output indicative of the quality of the liquid.

24. The system as recited in claim 5 further comprising means for measuring the time required for the liquid to travel between two predefined positions in the test medium; wherein the system further comprises means for communicating the measured time to a microprocessor connected to the system, said microprocessor stores measured time, uses said time as an input to a correlation algorithm or set of equations and provides an output on the polymer compounds of the oil, on the polar compounds of the oil, on a combined quality characteristic including polar and polymer compounds in an oil, frying oil quality, frying oil quality deterioration level with respect to regulations and recommendations by authorities for frying oil use and replacement or frying oil discarding time; and provides an output indicative of the quality of the liquid.

25. The system as recited in claim 5 wherein the test medium has at least two marks along the expected penetration track of the liquid; wherein the test medium is of light color and/or the liquid is colored so that the penetration front can be visually detected; wherein the distance between said marks is set according to the distance a liquid of a given quality attribute would penetrate the test medium for a given time; wherein the lower part of the test medium is put in contact with the higher part of the liquid; wherein the liquid is allowed to penetrate from the lower said mark for said given time and when said time elapses the position of the liquid front is compared with one of said marks in order to determine a liquid quality attribute.

26. A system for measuring a quality attribute of a liquid including oils, frying oils, edible oils, fats, shortenings and mixtures thereof comprising:
(a) a test medium having one single pore of capillary dimensions or interconnected pores of capillary dimensions; wherein the test medium presents a contact angle lower than ninety degrees with the liquid under examination, it is light colored and disposable and has two marks indicating beginning and end of liquid penetration;
(b) a liquid container for receiving the sample with a shape and size such that the liquid level does not drop significantly during liquid penetration in the test medium;
(c) means for measuring and controlling the temperature of said liquid including at least a temperature probe, a temperature controller and a heater combined with means for informing the user that the liquid has reached the desired temperature in order to start the measurement;
(d) means for holding the test medium, setting the position of the test medium and putting a portion of said test medium into contact with the liquid under examination so that the liquid penetrates the test medium; wherein the test medium is contacted with the liquid at said mark indicating the beginning of liquid penetration;
(e) means for measuring the rate of liquid penetration including a timer, means for starting the timer when the test medium has been put in contact with said liquid and means for stopping the timer when liquid reaches said mark indicating the end of penetration.
(f) microprocessor connected to the timer; wherein the measured time is communicated to the microprocessor, said microprocessor stores measured time, uses said time for calculations of a liquid quality attribute and provides an output indicative of the quality of the liquid.
(g) means for informing the user regarding the results of the measurement connected to the microprocessor.

* * * * *